US006827945B2

(12) United States Patent
Rosenbloom

(10) Patent No.: US 6,827,945 B2
(45) Date of Patent: Dec. 7, 2004

(54) NUTRITIONAL SUPPLEMENTS AND METHODS OF USING SAME

(75) Inventor: Richard A. Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 0 days.

(21) Appl. No.: 10/421,276

(22) Filed: Apr. 23, 2003

(65) Prior Publication Data

US 2003/0185918 A1 Oct. 2, 2003

Related U.S. Application Data

(60) Division of application No. PCT/US02/24794, filed on Aug. 6, 2002, which is a continuation-in-part of application No. 10/122,991, filed on Apr. 15, 2002, now Pat. No. 6,596,313, which is a continuation-in-part of application No. 09/923,090, filed on Aug. 6, 2001, now Pat. No. 6,592,896.

(51) Int. Cl.$^7$ .............................. A61K 9/10; A61K 9/14; A61K 9/20; A61K 9/48; A61K 35/78

(52) U.S. Cl. ...................... 424/464; 424/49; 424/434; 424/435; 424/440; 424/441; 424/451; 424/489; 424/756; 514/825; 514/937; 514/944

(58) Field of Search .......................... 424/464, 49, 434, 424/435, 440, 441, 451, 489, 756, 465, 439, 455

(56) References Cited

U.S. PATENT DOCUMENTS

| | | |
|---|---|---|
| 5,120,538 A | 6/1992 | Oei |
| 5,248,504 A | 9/1993 | Friedman |
| 5,385,734 A | 1/1995 | Friedman |
| 5,401,504 A | 3/1995 | Das et al. |
| 5,494,668 A | 2/1996 | Patwardhan |
| 5,707,630 A | 1/1998 | Morrow |
| 5,861,415 A | 1/1999 | Majeed et al. |
| 5,916,565 A * | 6/1999 | Rose et al. .................. 424/756 |
| 6,174,542 B1 | 1/2001 | Hinton et al. |
| 6,355,262 B1 * | 3/2002 | Krentz ......................... 424/401 |
| 6,596,313 B2 * | 3/2002 | Rosenbloom ............... 424/464 |

OTHER PUBLICATIONS

Chainani–Wu, "Safety and Anti–Inflammatory Activity of Curcumin: A Component Of Tumeric (*Curcuma longa*)" *J Altern Complement Med.* Feb. 2003;9(1):161–8 Abstract.
Sreejayan, "Nitric Oxide Scavenging By Curcuminoids" *J Pharm Pharmacol.* Jan. 1997;49(1):105–7 Abstract.
Singh, "Activation Of Transcription Factor NF–kappa B Is Suppressed By Curcumin (Diferuloylmethane)" *J Biol Chem.* Oct. 20, 1995;270(42):24995–5000 Abstract.
Chann et al., "In Vivo Inhibition Of Nitric Oxide Synthase Gene Expression By Curcumin, A Cancer Preventive Natural Product With Anti–Inflammatory Properties" *Biochem Pharmacol.* Jun. 15, 1998;55(12):1955–62 Abstract.

Ramsewk et al., "Cytotoxicity, Antioxidant And Anti–Inflammatory Activities Of Curcumins I–III From Curcuma Longa" *Phytomedicine.* Jul. 2000;7(4):303–8 Abstract.
Hamilton, "Tumour Necrosis Factor–Alpha Blockade: A New Era For Effective Management of Rheumatoid Arthritis." *Expert Opin Pharmacother* Jul. 2000;1(5):1041–52 Abstract.
Bharti, et al., "Curcumin (Diferuloylmethane) Down–Regulates the Constitutive Activation Of Nuclear Factor–Kappa B And IkappaBalpha Kinase In Human Multiple Myeloma Cells, Leading To Suppression Of Proliferation And Induction of Apoptosis" *Blood* Feb. 1, 2003;101(33):1053–62 Abstract.
Liacini, et al., Induction Of Matrix Metalloproteinase–13 Gene /Expression By TNF–Alpha Is Mediated by MAP Kinasees, Ap–1, and NF–KappaB Transcription Factors In Articular Chondrocytes *Exp Cell Res.* Aug. 1, 2003;288(1):208–17 Abstract.
Banerjee, et al., Modulation Of Inflammatory Mediators By Ibuprofen And Curcumin Treatment During Chronic Inflammation In Rat *Immunopharmacol Immunotoxicol.* May 2003; 25(2): 213–24 Abstract.
Bremner, Natural Products As Targeted Modulators Of The Nuclear Factor–KappaB Pathway *J Pharm Pharmacol.* Apr. 2002; 54(4): 453–72 Abstract.
Ahmed, et al., Green Tea Polyphenol Epigallocatechin–3–Gallate(EGCG) Differentially Inhibits Interleukin–1 {Beta}–Induced Expression Of Matrix Metalloproteinases–1 And—13 In Human Chondrocytes *J Pharmacol Exp Ther.* Nov. 4, 2003 Abstract.

(List continued on next page.)

*Primary Examiner*—James M. Spear
(74) *Attorney, Agent, or Firm*—Knoble Yoshida & Dunleavy LLC

(57) ABSTRACT

A nutritional supplement for providing, and for promoting the health of salivary glands and/or supporting normal or healthy swallowing includes ingredients obtainable from turmeric, ginger, and horseradish. The nutritional supplement may also be used to treat symptoms such as symptoms of a common cold, sore throat, congestion, mucositis, laryngitis, mucous membrane inflammation and sialorrhea, as well as inflammation and viral infectin, or to inhibit or exterminate a virus. This nutritional supplement can be orally administered a person. The nutritional supplement may further include optional ingredients such as ingredients obtainable from slippery elm bark powder and green tea, as well as other optional ingredients. This nutritional supplement may further include a pharmaceutically acceptable carrier for oral administration.

Also disclosed are methods of providing nutrition, for promoting the health of salivary glands and/or supporting normal or healthy swallowing, as well as methods for treating symptoms of a common cold, sore throat, congestion, mucositis, laryngitis, mucous membrane inflammation and sialorrhea. Methods of treating inflammation, and viral infections, as well as inhibiting or exterminating viruses are also disclosed.

20 Claims, No Drawings

OTHER PUBLICATIONS

Ahmed, et al., Green Tea Polyphenol Epigallocatechin–3–Gallate Inhibits The IL–beta–Induced Activity And Expression Of Cyclooxygenase–2 And Nitric Oxide Synthase–2 In Human Chrondrocytes *Free Radic Biol Med.* Oct. 15, 2002; 33(8): 1097–105 Abstract.

Paleolog et al., Angiogenesis In Arthritis: Role In disease Pathogenesis And As A Potential Therapeutic Target *Angiogenesis 2* (4): 295–307 Citation.

Carlevaro, et al., Vascular Endothelial Growth Factor (VEGF) In Cartilage Neovascularisation And Chondrocyte Differentiation: Auto–paracrine Role During Endochondral Bone Formation *J Cell Sci 2000*, 113:59–69.

Vascular Endothelial Growth Factor (VEGF).

Klimiuk et al, Soluble Adhesion Molecules (ICAM–1, VCAM–1, and E–Selectin) And Vascular Endothelial Growth Fctor (VEGF) In Patients W ith Distinct Variants Of Rheumatoid Synovitis *Annals of the Rheumatic Diseases 2002*;61:804–809.

Internet download, Prinz et al., "Saliva Tannin interactions", *J. Oral Rehabil,* Nov. 2000; 27(11) :991–4.

Internet download; Bacon et al., "Binding affinity of hydrolysable tannins to parotid saliva and to proline–rich proteins derived form it", *J. Agric Food Chem* Mar. 2000; 48(3) : 838–43.

Internet download; Lomniczi et al., "Inhibition of salivary secretion by lipopolysaccharide: possible role of prostaglandins", *Am J. Physiol Endocrinol Metabm* Aug. 2001; 281.

Internet download; Brouet et al., "Curcumin an anti–tumour promoter and anti–inflammatory agent, inhibits induction of nitric oxide synthase in activated macrophages", *Biochem Biophys Res Commun* Jan. 17, 1995; 206.

Internet download, Rettori et al., "Control of salivary secretion by nitric oxide and its role in neuroimmunomodulation", *Ann NY Acad Sci* 2000; 917:258–67.

Internet download, Tjendraputra et al., "Effect of Ginger Constituents and Synthetic Analogues on Cyclooxygenase–2 Enzyme in Intact Cells", *Bioorg Chem* Jun. 2001;29(3):156–163.

Internet article; ALS Survival Guide, Treatment for ALS; Feb. 5, 2002, pp. 1–15; lougehrigsdisease.net/als.

Park, "Sialorrhea, "The Drooling Patient"", Loyola University Health System, The Department of Otolaryngology Head & Neck Surgery, pp. 1–3, luhs.org/depts./otolaryn/P_peds1.htm.

Salzer, "Sialorrhea", Grand Rounds Archive at Baylor, The Bobby r. Alford Department of Otorhinolaryngology and Communicative Sciences, 1–3.

Rettori et al., "Control of Salivary secretion by nitric oxide and its role in neuroimmunomodulation", *Ann NY Acad Sci* 2000;917:258–67.

Mier et al., "Treatment of Sialorrhea with glycopyrrolate A Double–blind, Dose–Ranging Study", *Pediatrics & Adolescent Medicine,* vol. 154, No. 12, Dec. 2000.

Internet page, "Where are your salivary glands?",.cfm American Academy of Otolaryngology—Head and Neck Surgery, entnet.org/healthinfo/throat/salivary.

Legeza, et al., "Prostaglandins—their role in the mechanisms of the development of the primary reaction to radiation syndrome", *Radiats Biol Radioecol* Jan.–Feb. 1994;34(1):32–8.

Novozhenov, et al., "Changes in lipid peroxidation and the antioxidant system in patients with acute radiation sickness", *Voen Med Zh* Apr. 1993;(4):38–40, 80 Abstract.

Chaialo, et al., "Free–radical processes and blood antioxidant systems in the late period following acute radiation sickness", *Med Radiol* (*Mosk*) 1991;36(5):20–1 Abstract.

Bazhan, "Lipid peroxidation and the antioxidant system in subjects exposed to the influence of extreme factors", *Lik Sprava* Dec. 1998;(8):47–50 Abstract.

Beckman, et al., "Radiation therapy impairs endothelium-dependent vasodilation in humans", *J Am Coll Cardiol* Mar. 1, 2001;37(3):761 Abstract.

Castillo, et al., "Antiosidant activity and radioprotective effects against chromosomal damage induced in vivo by X–rays of flavan–3–ols (Procyanidins) from grape seeds (*Vitis vinifera*): comparative study versus other phenolic and organic compounds", *J Agric Food Chem* May 2000;48(5):1738–45 Abstract.

Weiss, et al., "Radioprotection by antioxidants", *Ann N Y Acad Sci* 2000;899:44–60 Abstract.

Weiss, "Pharmacologic approaches to protection against radiation–induced lethality and other damage", *Environ Health Perspect* Dec. 1997;105 Suppl6:1473–8 Abstract.

Baraboi, et al., "Mechanism of the antistressor and antiradiation action of plant phenol compounds", *Ukr Biokhim Zh* Nov.–Dec. 1998;70(6):13–23 Abstract.

Wu, et al., "Synthesis and bio–activity of coumarin derivatives and studies on its relationships between activity and lipophilicity", *Yao Xue Xue Bao* 1993;28(4):266–72 Abstract.

Thresiamma, et al., "Protective effect of curcumin, ellagic acid and bixin on radiation induced toxicity", *Indian J Exp Biol* Sep. 1996;34(9):845–7 Abstract.

Deneke, "Thiol–based antioxidants", *Curr Top Cell Regul* 2000;36:151–80 Abstract.

Il'iuchenok, et al., "Pharmacological and radioprotective properties of some gamma–pyrone derivatives (flavanones and flavanols)", *Farmakol Toksikol* Sep.–Oct. 1975;38(5):607–12.

Kapitanov, et al., "Radiation–protective effectiveness of lycopene", *Radiats Biol Radioecol* May–Jun. 1994;34 (3):439–45 Abstract.

Beliaev, et al., "Modification of the body's resistance to acute ionizing radiationby synthetic beta–carotene", *Vopr Med Khim* Nov.–Dec. 1992;38(6):39–42 Abstract.

Chigareva, et al., "Radio–protective effect of sulfur–containing methylfuran derivatives and the role of thiols in its realization", *Radiobiologiia* Nov.–Dec. 1983;23(6):816–9 Abstract.

Samoilov, et al., "The radioprotective and antioxidant properties of solubilized alpha–tocopheraol acetate", *Eksp Klin Farmakol* Jul.–Aug. 1992;55(4):42–4 Abstract.

Kamat, et al., "Chlorophyllin as an effective antioxidant against membrane damage in vitor and ex vivo", *Biochim Biophys Acta* Sep. 27, 2000;1487(2–3):113–27 Abstract.

Internet download, "1001 Herbs for a Healthy Life" 2001, 1001 Herbs; pges 1 and 2.

Internet download, "Slippery Elm", MotherNature.com Health Encyclopedia, 1995–2002, MotherNature.com Inc., pges 1 and 2.

Uma, et al., "Radiation protection by the ocimum flavonoids orientin and vicenin: mechanisms of action", *Radiat Res* Oct. 2000; 154(4):455–60 Abstract.

Moskalenko, et al., "The role of immunological mechanisms in the development of the late sequelae of nuclear disasters", *Lik Sprava* Jun. 1999;(4):3–8 Abstract.

Ovsiannikova, et al., "Efficacy of antioxidant preparations used for correction of impairment of oxidative homeostasis in Chernobyl liquidators", *Radiats Biol Radioecol* Mar.–Jun. 1999;39(2–3):318–21, Abstract.

Spector, et al., "Reduction of x–radiation mortality by cabbage and broccoli", *Proceedings of the Society of Experimental Biology and Medicine* 100:405–407 Citation.

Calloway, et al., "Further studies of the influence of diet on radiosensitivity of guinea pigs, with special reference to broccoli and alfalfa", *Journal of Nutrition* 19:340–348 Citation.

Chlorophyll as Therapy; 4:1–5; www.wheatgrass.com/book/chapter4.html.

Gamma Ray Irradiation; "Research finds chorella may offer protection against gamma–ray irradiation", www.healthbooks.com/PressRoom/Gamma.html; 1–2.

Antioxidants; "Also Known as: Free Radical Scavengers; Oxidative Scavengers", www.alternativehealth.com.au/antioxid.html; 1–9.

Goodman, "Protection From Heavy Metal and Radiation Poisoning", *GERMANIUM–The health and life enhancer*, 5:1–8.

Afanas'ev, et al., "Chelating and free radical scavenging mechanisms of inhibitory action of rutin and quercetin in lipid peroxidation", *Biochem Pharmacol* Jun. 1, 1989;38(11):1763–9 Abstract.

Ishige, et al., "Flavonoids protect neuronal cells from oxidative stress by three distinct mechanisms", *Free Radic Biol Med* Feb. 15, 2001;30(4):433–46 Abstract.

Shobana, et al., "Antioxidant activity of selected Indian spices", Prostaglandins Leukot *Essent Fatty Acids* Feb. 2000;62(2):107–10 Abstract.

Tiukavkina, et al., "Dihydorquercetin—anew antioxidant and biologically active food additive", Vopr Pitan 1997;(6):12–5 Abstract.

Plumb, et al., "Antioxidant properties of flavonal glycosides from tea", *Redox Rep* 1999;4(1–2):13–6 Abstract.

Skaper, et al., "Quercetin protects cutaneous tissue–associated cell types including sensory neurons from oxidative stress induced by glutathione depletion: cooperative effects of ascorbic acid", *Free Radic Biol Med* 1997;22(4):669–78 Abstract.

Jones, et al., "Radioprotective effect of free radical scavenging enzymes", *J Otolaryngol* Oct. 1990;19(5):299–306 Abstract.

Boloor, et al., "Chlorophyllin as a protector of mitochondrial membranes against gamma–radiation and photosensitization", *Toxicology* Nov. 30, 2000;155(1–3):63–71 Abstract.

Kim, et al, "In vivo radioprotective activity of Panax ginseng and diethyldithiocarbamate", In Vivo Sep.–Oct. 1993;7(5):467–70 Abstract.

Rice–Evans, et al., "The relative antioxidant activities of plant–derived polyphenolic flavonoids", Free *Radic Res* 22:4:375–83 1995 Summary.

Gillis, "Panax ginseng pharmacology: a nitric oxide link", *Biochemical Pharmacology* 54:1–8 (1997) Summary.

Duke, et al., "Biological Activities of CURCUMINOIDS", Phytochemical and Ethnobotanical Database.

Robak, et al., "Bioactivity of flavonoids", *Pol J Pharmacol* Nov.–Dec. 1996;48(6):555–64 Abstract.

Bursel, et al., "Can protein kinase C inhibition and vitamin E prevent the development of diabetic vascular complications?", *Diabetes Res Clin Pract* Sep. 1999;45(2–3):169–82 Abstract.

Freedman, et al., "Select flavonoids and whole juice from purple grapes inhibit platelet functionand enhance nitric oxide release", *Circulation* Jun. 12, 2001;103(23):2792–8 Abstract.

Lin, et al., "Recent studies on the biofunctions and biotransformations of curcumin", *Biofactors* 2000;13(1–4):153–8 Abstract.

Isoherranen, et al., "Ultraviolet irradiation induces cyclooxygenase–2 expression in keratinocytes", *Br J Dermatol* Jun. 1999;140(6):1017–22 Abstract.

Duarte, et al., "Vasodilator effects of quercetin in isolated rat vascular smooth muscle", *Eur J Pharmacol* Aug. 1993 239:1–7 Abstract.

Giugliano, et al., "Oxidative stress and diabetic vascular complications", *Diabetes Care* Mar. 1996;19(3):257–67 Abstract.

On, et al., "Vitamin c prevents radiation–induced endothelium–dependent vasomotor dysfunction and de–endothelialization by inhibiting oxidative damage in the rat", *Clin Exp Pharmacol Physiol* Oct. 2001;28(10):816–21 Abstract.

Konopacka, et al., "Modifying effect of vitamins C, E and beta–carotene agaist gamma–ray–induced DNA damage in mouse cells", *Mutat Res* Sep. 11, 1998;417(203):85–94 Abstract.

Shope, "Radiation–induced skin injuries from fluoroscopy", Scientific Exhibit 060PH at the 81$^{st}$ Scientific Assembly and Annual Meting of the Radiological Society of North America, Nov. 26–Dec. 1, 1995, Radiology vol. 197(P) Supplement, P449 Abstract.

Noble–Adams, "Radiation–induced skin reactions. 2: Development of a measurement tool", Br J Nurs Oct. 14–27, 1999;8(18):1208–11 Abstract.

Noble–Adams, "Radiation–induced skin reactions. 3: Evaluating in RISRAS", *Br J Nurs* Oct. 28–Nov. 10 1999;8(19):1305–12 Abstract.

Cusma, et al., "Real–time measurement of radiation exposure to patients during diagnostic coronary angiography and percutaneous interventional procedures", *J Am Coll Cardiol* Feb. 1999;33(2):427–35 Abstract.

DOE Openness: Human Radiation Experiments: Roadmap to the Project, ACHRE Report , "How Does Radiation Affect Humans", pp. 1–5 at http://tis.eh.doe.gov/ohre/roadmap/achre/intro.

DOE Openness: Human Radiation Experiments: Roadmap to the Project, ACHRE Report, "What is Ionizing Radiation?", pp. 1–3 at http://tis.eh.doe.gov/ohre/roadmap/achre/intro.

Newall et al., "The control of oral secretions in bulbar ALS/MND", *J. Neurol Sci*, Aug. 1996 vol. 139 Supp;:43–44.

Morgan et al., "Topical treatment of radiation induced dermatitis with N–acetylcysteine (NAC)(Meeting Abstract)", *Proc Annu Meet Am Assoc Cancer Res*, 1996; 37:A4142.

William F. Dial, *Cosmetic Dermatology*, "Topical Vitamin C May Help Protect Skin From UV Damage", Dec. 1991, pp. 34–35.

Bernard Idson, College of Pharmacy, University of Texas at Austin, Ultraviolet Irradiation Injury and Repair, Jan. 1992, pp. 22–24 and pp. 81–81.

Bissett et al., "J. Soc. Cosmet. Chem., Protective effect of a topically applied anti–oxidant plus an anti–inflammary agent against ultraviolet radiation–induced chronic skin-damage in the hairless mouse", 43, Mar./Apr. 1992, pp. 85–92.

Darr et al., *British Journal of Dermatology*, "Topical vitamin C protects porcine skin from ultraviolet radiation–induced damage" (1992) 127, 247–253.

*Dermatology Times*, "New Aqueous Vitamin C blocks UV rays" 1991.

Fuchs et al., "Acute Effects of Near Ultraviolet and Visible Light on the Cutaneous Antioxidant Defense System"Oct. 3, 1988, pp. 739–744.

Vitamin E (Tocopherol) vs. Vitamin E Acetate, Roche, Jun. 1991.

Schmuth, et al., "Permeability barrier function of skin exposed to ionizing radiation" Arch Dermatol Aug. 2001; 137(8);1019–23.

Katiyar, et al., "Green tea polyphenol (−)–epigallocatechin–3–gallate treatment of human skin inhibits ultraviolet radiation–induced oxidative stress" Carcinogenesis Feb. 2001; 22(2):287–94.

Vitamin D–3 400 I.U.—The Way Up (http://www.thewayup.com/products/0028.htm).

* cited by examiner-

NUTRITIONAL SUPPLEMENTS AND METHODS OF USING SAME

This application is a divisional of International patent application no. PCT/US02/24794, filed on Aug. 6, 2002 designating the United States and currently, which, in turn, is a continuation-in-part of U.S. patent application Ser. No. 10/122,991, filed on Apr. 15, 2002, now U.S. Pat. No. 6,596,313 which, in turn, is a continuation-in-part of U.S. patent application Ser. No. 09/923,090, filed on Aug. 6, 2001, now U.S. Pat. No. 6,592,896.

BACKGROUND OF THE INVENTION

A. Field of the Invention

The present invention relates to a nutritional supplement and methods of using it. More particularly, the present invention relates to a nutritional supplement useful for promoting various health effects and to methods for administering the nutritional supplement for at least these purposes.

B. Description of the Prior Art

Treatment of Sialorrhea

Sialorrhea, a symptom related to amyotrophic lateral sclerosis (ALS), and other causes such as achalasia, acoustic neuroma, Bell's palsy, cerebral palsy, cerebrovascular accident (stroke), glossopharyngeal neuralgia, Guillain-Barre syndrome, hypocalcemia, Ludwig's angina, mental retardation, motor-neuron disease, muscular dystrophy, myasthenia gravis, myotonic dystrophy, paralytic poliomyelitis, polymyositis, Parkinson's disease, Radical Cancer surgery, Seventh-nerve palsy, Shy-Drager syndrome, and Wilson's disease, is the excessive drooling due to salivary gland dysfunction such as overproduction of saliva from the salivary glands. Sometimes, sialorrhea may also be induced by drugs such as clonazepam, ethionamide, haloperidol, and transdermal nicotine among others. Sialorrhea may also be caused by abnormal or unhealthy swallowing by a patient suffering from diseases such as ALS.

Much effort has been made to treat Sialorrhea. Newall et al. reported using beta antagonists to control excessive secretions of the oral salivary glands and reported a 75% success rate (*J. Neurol. Sci.*, 1996, 139, 43–4). Mier et al have found that ingestion of glycopyrrolate is effective in treating sialorrhea in children. However, 20% of the children treated with glycopyrrolate experienced substantial adverse effects, enough to require discontinuation of the medication (*arch. Pediatr. Adolesc. Med.*, 2000, 154, 1214–1218). According to a recent study by Rettori et al. (*Ann. N. Y. Acad. Sci.*, 2000; 917; 258–67), inhibitors of nitric oxide synthase (NOS) decrease stimulated salivary secretions whereas donors of NOS potentiate stimulated salivary secretions. This indicates that nitric oxide exerts a stimulatory role on salivary secretion.

Treatment of Inflammation

In modern non-herbal medicine, there are two major categories of anti-inflammatory medicines: steroidal and non-steroidal. Steroidal anti-inflammatory medicines are powerful medications, which are based on hormonal substances, such as cortisone. Steroidal medications have a stronger anti-inflammatory response than non-steroidal medicines. Steroidal medications can be taken as pills, injected into the bloodstream, or injected directly into a joint space. There are many non-steroidal anti-inflammatory medications. Acetaminophen, aspirin, ibuprofen, and naproxen are the most commonly used non-steroidal anti-inflammatory medications.

Non-steroidal anti-inflammatory drugs have three major actions, all of which are related to inhibition of cyclo-oxygenase resulting in decreased formation of prostanoids. Firstly, an anti-inflammatory action can be achieved by reducing production of vasodilator prostaglandins (PGE2, PGI2), which means less vasodilation and, indirectly less oedema. Secondly, an analgesic effect can be achieved by reduced prostaglandin production (less sensitization of nociceptive nerve endings to the inflammatory mediators bradykinin and 5-hydroxytryptamine). Thirdly, an antipyretic effect can produce an anti-inflammatory action, probably due to a decrease in the mediator PGE2 generated in response to inflammatory pyrogens, much as interleukin-1.

There are side effects to both of these groups of medicines. They may include, among other things, stomach upset, stomach bleeding, or ulcers, kidney problems, hearing problems and ankle swelling. Additionally, the steroidal anti-inflammatory medications can have more serious side effects including: loss of bone mass, cataracts, reduced ability to fight infection, swelling and weight gain, mood changes, high blood pressure, and problems with the bone marrow where blood cells are produced.

Turmeric (*Curcuma Longa*)

Turmeric, or Haldi in Hindi, is used very widely as medicine as well as a common ingredient in Indian cooking. The rhizome of turmeric is used in medicine and food as a fine powder.

Anti-inflammatory effects of curcumin isolated from *Curcuma longa* were reported in Srimal and Dhawan, Pharmacology of Diferuloyl Methane, a Non-steroidal Anti-inflammatory Agent, *J. Pharm. Pharmac.*, 25:447–452 (1973). Significant anti-inflammatory activity for curcumin, comparable with phenylbutazone and hydrocortisone, was observed by Arora et al. (*Indian Journal of Medical Research*, 1971, 59, 1289–1291). Curcumin, an alkaloid (diferuloyl methane) isolated from the alcoholic extract of turmeric, has been shown to be a potent anti-inflammatory agent. Further work on anti-inflammatory and anti-arthritic activity has also been carried out by Thatte et al. (*Indian Journal of Pharmacology*, 1986, 18 (1), 19–21). Turmeric has been found to have significant anti-inflammatory activity both in acute and chronic models. The therapeutic dose of turmeric, for optimal activity if used alone, is reported to be in the range of 5 to 10 grams of dry powder daily (Patwardhan, U.S. Pat. No. 5,494,668). This dosage level, however, can produce a feeling of nausea.

Curcumin not only has anti-inflammatory properties but also has anti-oxidant, anti-tumor and other valuable properties. When used in low concentrations, curcumin can inhibit nitric oxide synthase (NOS) and, therefore, inhibit nitric oxide production. For example, Brouet et al. (*Biochem. Biophys. Res. Commun.*, 1995 Jan. 17; 206 (2); 533–40) have reported that NOS activity in soluble extracts of macrophages activated for 6–24 hours in the presence of curcumin (10 microM) was significantly lower that that of macrophages activated without curcumin. Northern-blot and immunoblotting analyses demonstrated that significantly reduced levels of the mRNA and 130-k Da protein of inducible NOS were expressed in macrophages activated with curcumin, compared to those without curcumin activation. Inhibition of NOS induction was maximal when curcumin was added together with lipopolysaccharide (LPS) and interferon-gamma (IFN-gamma) and decreased progressively as the interval between curcumin and LPS/IFN-gamma was increased to 18 hours.

Ginger (*Zingiber Officinale*)

Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

Chinese medical texts from the fourth century B.C. suggest that ginger is effective in treating nausea, diarrhea, stomach aches, cholera, toothaches, bleeding, and rheumatism. Ginger was later used by Chinese herbalists to treat a variety of respiratory conditions, including coughs and the early stages of colds.

Ginger's modern use dates back to the early 1880s, when a scientist named D. Mowrey noticed that ginger-filled capsules reduced his nausea during an episode of flu. Inspired by this, he performed the first double-blind study of ginger. Germany's Commission E subsequently approved ginger as a treatment for indigestion and motion sickness. Ginger has become widely accepted as a treatment for nausea. Even some conventional medical texts suggest ginger for the treatment of the nausea and vomiting of pregnancy, although others are more cautious.

Ginger gives relief from muscular discomfort and pain. It inhibits prostaglandin and leukotriene biosynthesis and histamine release. Thus it acts as an anti-inflammatory as well as an antacid agent. It is a dual inhibitor of the lipoxigenase and cycloxigenase system. Ginger contains 1–4% essential oil (oleoresin). Used alone fresh Ginger is required to be used in substantially high doses (50 grams daily), which is not only inconvenient but can act as an irritant to the gastric mucosa. In dry form for any significant results, 7 to 10 grams of dry ginger powder has to be taken daily. Such large doses of ginger are extremely inconvenient for the patient and affect patient compliance on a daily basis. (See Potwardhan, U.S. Pat. No. 5,494,668.)

Horseradish (*Armoracia Rusticana*)

Horseradish, a perennial herb (*Armoracia rusticana*, but sometimes classified in other genera) of the family Cruciferae (mustard family), is native to Central and Southern Europe where it has long been cultivated in gardens and naturalized in many parts of North America. It is grown mainly for its roots, which formerly were used medicinally, particularly as an antiscorbutic. Horseradish is also an excellent diuretic, and is good for digestion problems. Herbalists combine horseradish and honey for coughs and asthma treatments. Externally, it is sometimes used to alleviate the pain and stiffness caused by rheumatism.

Friedman, U.S. Pat. Nos. 5,248,504 and 5,385,734, has used horseradish to treat nasal and sinus dysfunction. Attempts have also been made to provide oral horseradish remedies for certain ailments. Mays, U.S. Pat. No. 98,875, relates to a medical compound for alleviating asthma, coughs and colds. The compound includes pulverized horseradish. Diets, U.S. Pat. No. 74,205, discloses a medical compound containing horseradish for the treatment of consumption.

Slippery Elm (*Ulmus Rubra*)

Slippery elm trees are native to North America. Slippery Elm has been employed in traditional herbal medicine for over 100 years. The dried inner portion of the slippery elm bark has been used both by Native Americans and early settlers. Slippery Elm is a nutritious food that was made into a type of pudding for those who had weak stomachs. Slippery Elm is soothing to irritated tissues and has been used in poultices for its ability to encourage healing in wounds. Slippery Elm nourishes the adrenal glands, gastrointestinal tract, and respiratory system. It helps the body expel excess mucus. Other conditions, for which slippery elm is used, include: abscess, broken bones, burns and scalds, cholera, colitis, constipation in children, debility, diaper rash, diarrhea in children, diverticulitis, dysentery, hemorrhoids, hiatal hernia, indigestion, labor pain, leprosy and sore throat.

Green Tea (*Camellia Sinensis*)

Green tea is the dried leaves and leaf buds of the shrub *Camellia sinensis*. It is mainly produced in China and Japan. Dried tea leaves are composed mainly of phytochemicals known as polyphenols (36%), principally flavonols (including catechins), flavonoids, and flavondiols. The leaves also contain plant alkaloids (about 4%), including caffeine, theobromine and theophylline. Much of the research on green tea has been focused on its potential to prevent cancer. Research suggests that the polyphenols in green tea are responsible for a chemopreventive effect (E. Kaegi, *Canadian Medical Association Journal*, 1998, 158: 1033–35).

It is an object of certain embodiments of the present invention to provide a nutritional supplement to promote the health of salivary glands and/or to support normal or healthy swallowing.

It is a further object of certain embodiments of the present invention to provide a composition for treating sialorrhea.

It is still a further object of certain embodiments of the present invention to provide a composition for treating some common types of inflammation such as sore throat, congestion, laryngitis and mucous membrane inflammation.

It is still a further object of certain embodiments of the present invention to provide a method to treat a sore throat, congestion, laryngitis and mucous membrane inflammation by administering a composition made from natural herbs.

It is still a further object of certain embodiments of the present invention to provide a method to treat sialorrhea by administering a composition made from natural herbs.

It is a still further object of certain embodiments of the present invention to provide a nutritional supplement with virucidal and/or virustatic properties.

These and other objects of the present invention will be apparent from the summary and detailed description of the invention, which follow.

SUMMARY OF THE INVENTION

In a first aspect, the present invention relates to a nutritional supplement. The nutritional supplement of the invention may be used for providing nourishment, or, optionally for promoting the health of salivary glands and/or supporting normal or healthy swallowing. The nutritional supplement includes ingredients, which can be obtained from turmeric, ginger and horseradish. It has been found that the combination of these ingredients provides a nutritional supplement that provides a nutritional benefit and is effective in promoting the health of salivary glands and/or supporting normal or healthy swallowing.

In a second aspect, the present invention relates to a method of promoting the health of salivary glands and/or supporting normal or healthy swallowing, by administering an effective amount of the nutritional supplement of the present invention.

In a third aspect, the present invention relates to a method to treat one or more of a common cold, and/or one or more symptoms thereof, a sore throat, congestion, laryngitis, mucositis, mucous membrane inflammation and sialorrhea, by orally administering to a patient an effective amount of a composition including ingredients which can be obtained from turmeric, ginger and horseradish, which provides substantial relief from one or more of these symptoms or ailments.

In a fourth aspect, the present invention relates to a method of inhibiting the growth of a virus by administering to a carrier carrying the virus, a composition including ingredients which can be obtained from turmeric, ginger and horseradish.

In a fifth aspect, the present invention relates to a method of treating viral infection by administering a composition including ingredients which can be obtained from turmeric, ginger and horseradish.

In a sixth aspect, the present invention relates to a method of treating inflammation by administering a composition including ingredients which can be obtained from turmeric, ginger and horseradish.

DETAILED DESCRIPTION OF THE PREFERRED EMBODIMENTS

In a first aspect, the present invention relates to a nutritional supplement. The nutritional supplement may be employed for the purpose of providing nourishment. Alternatively, the nutritional supplement of the present may provide some additional benefits such as promoting the health of salivary glands and/or supporting normal or healthy swallowing. The nutritional supplement of the present invention includes ingredients, which can be obtained from turmeric, ginger, and horseradish.

By "nutritional" or "nutritional supplement" as used herein is meant that the supplements used in the practice of this invention provide a nourishing amount of one or more ingredients derived from turmeric, ginger and horseradish.

As used herein the term "flavors" includes both fruit and botanical flavors.

As used herein the term "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term "pharmaceutically acceptable" means a component that is suitable for use with humans and/or animals without undue adverse side effects (such as toxicity, irritation, and allergic responses), commensurate with a reasonable risk/benefit ratio. Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

Each of turmeric, ginger, or horseradish contain active ingredients which may provide some beneficial effect in promoting the health of salivary glands, supporting normal or healthy swallowing, and/or treating one or more symptoms including symptoms of a common cold, a sore throat, congestion, laryngitis, mucositis and mucous membrane inflammation. Turmeric and ginger may further serve as COX-2 inhibitors to treat certain types of inflammation such as that due to arthritis. However, the taste of each of turmeric, ginger, or horseradish at an effective dosage level may be too overpowering for a patient. It has been found that the combination of materials, which can be obtained from turmeric, ginger and horseradish, in the nutritional supplement of the present invention provides a substantial beneficial effect, as well as favorable taste characteristics which make the nutritional supplement palatable.

The first ingredient of the nutritional supplement of the present invention may be obtained from turmeric. The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis by *Chromatography and Microscopy*, p. 169, Ann Arbor Science Inc., 1973). The essential oils of turmeric (*curcuma longa*) are primarily composed of the following compounds: d-camphor (1%), cyclo-isoprenemyrcene (85%), and p-tolylmethylcarbinol (5%), (see E. Gunther, *The Essential Oil*, pp. 123–4, Van Nostrand Co., 1955).

The first ingredient of the nutritional supplement of the present invention, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane) and mixtures of two or more of these curcuminoids.

Methods for isolating curcuminoids from turmeric are known, (see Janaki and Bose, An Improved Method for the Isolation of Curcumin From Turmeric, J. Indian Chem. Soc. 44:985 (1967)). Alternatively, curcuminoids for use in the present invention can be prepared by synthetic methods.

The first ingredient, which can be obtained from of turmeric, can be incorporated into the nutritional supplement of the present invention in a variety of different forms. Those different forms preferably include extracts of turmeric such as turmeric powder extracts, turmeric fluid extracts, one or more the curcuminoid compounds, and turmeric powder, parts of, or whole plants of turmeric, tinctures thereof, and mixtures thereof. More preferably, the first ingredient is a turmeric extract.

The second ingredient of the nutritional supplement of the present invention may be obtained from ginger (also commonly called ginger root). Ginger inhibits prostanoid synthesis and also products of 5-lipoxygenase. The potency of the ginger extract in the acute inflammation test appears to be comparable to that exhibited by acetyl salicylic acid reported in the same study. (Mascolo N. et al *Journal of Ethnopharmocology*, 1989, 27, 129–140).

One of the features of inflammation is increased oxygenation of arachidonic acid, which is metabolized by two enzymic pathways—the cyclooxygenase (CO) and the 5-lipoxygenase (5-LO)-leading to the production of prostaglandins and leukotrienes respectively. It is suggested (Srivastava and Mustafa; *Medical Hypotheses*, 1992, 39 342–348) that at least one of the mechanisms by which ginger shows its ameliorative effects could be related to inhibition of prostaglandin and leukotriene biosynthesis, i.e. it works as a dual inhibitor of eicosanoid biosynthesis.

Ginger contains 1–4% essential oil (oleoresin). Many chemical investigations have been carried out on the constituents of the essential oil of ginger. All together more than 200 different volatiles have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The second ingredient of the nutritional supplement of the present invention, which may be obtained from ginger, can be incorporated in the nutritional supplement of the present invention in many different forms including extracts such as ginger powder extracts, ginger fluid extracts, ginger powder including ginger root powder, and one or more active compounds of ginger, parts of, or whole ginger plants, tinctures thereof, and mixtures thereof. Also, for any specific active compound of ginger for which suitable synthesis routes are known, the active compound can be prepared synthetically. Preferably, the second ingredient of the nutritional supplement of the present invention is selected from ginger extract, and ginger root powder.

A third ingredient of the nutritional supplement of the present invention may be obtained from horseradish, also commonly called horseradish root. Horseradish's pharmacological activities are mainly due to its active compounds. The active compounds of horseradish which may be useful in the present invention include, but are not limited to, allyl-isothiocyanate, amylase, arginine, ascorbic acid, asparagine, gentisic acid, kaempferol, limonene, niacin, p-hydroxy-benzoic acid, pectin, phenylpropyl-isothiocyanate, quercetin, raphanin, riboflavin, rutoside, selenium, sinapic acid, sinigrin, tannin, thiamin, vanillic acid and zinc, as well as mixtures of two or more of these compounds.

The third ingredient of the nutritional supplement of the present invention, which may be obtained from horseradish, can be included in the nutritional supplement in many different forms. Those different forms include horseradish powder, horseradish extracts such as horseradish powder extracts and horseradish fluid extracts; one or more active compounds of horseradish, parts of, or whole plants of horseradish, tinctures thereof, and mixtures thereof. For a particular active compound, for which a synthetic route is known, the active compound may be obtained synthetically. Preferably, the third ingredient of the nutritional supplement of the present invention is selected from horseradish powder and horseradish extract.

All active compounds of the present invention may be obtained from other sources, if available. Thus, the phrase "which can be obtained from" or the phrase "which may be obtained from" is meant to encompass compounds or nutritional supplements that are obtainable from turmeric, ginger, horseradish, slippery elm or green tea and therefore encompasses synthetic forms of the same compounds and/or compositions as well as the same compounds and/or compositions obtained from other sources.

The ingredients of the nutritional supplement of the present invention, which may be obtained from turmeric, ginger and horseradish, may be used in the forms of turmeric powder, ginger powder, and horseradish powder, each of which may be ground from the rhizome of turmeric, ginger root and horseradish root respectively. Alternatively, turmeric powder, ginger powder, horseradish powder, and/or one or more of the active compounds contained therein may be purchased from commercial sources such as Delavau Co. Alternatively, the ingredients of the present invention can be used in the form of turmeric extract, ginger extract and horseradish extract, which may be extracted from each of turmeric rhizome, ginger root and horseradish roots using common extraction procedures. One suitable extraction procedure is described below.

The extraction procedure comprises, generally, the steps of:

1) cleaning the plant from which the pharmacologically or biologically active plant extract is to be obtained to remove any foreign matter thereon;
2) particulating the plant to obtain a particulate mass having particle size ranging from 0.001 to about 10 mm$^3$; and
3) subjecting the particulate mass to at least one polar and at least one non-polar solvent to obtain separate fractions of plant extract soluble in the respective solvents, and mixing the fractions so obtained to obtain the beneficiated plant extract in accordance with this invention.

For instance, in the case of turmeric, the process comprises the steps of:

1) cleaning the roots of turmeric to remove any foreign matter thereon;
2) particulating the roots to obtain a particulate mass having particle size ranging from 0.001 to about 10 mm$^3$;
3) subjecting the particulate mass to distillation to obtain a volatile fraction, if any, from the particulate mass;
4) cooking the distilled particulate mass in a polar solvent, such as water to solubulize material in the distillation-treated particulate mass to obtain first solution and a first residue;
5) filtering the first solution from the first residue;
6) evaporating the filtrate obtained from the first solution to remove the solvent and obtain a solute designated as fraction A obtained from the particulate mass;
7) subjecting the first residue to treatment with a second polar solvent such as 75% to 95% ethanol for twelve to thirty-six hours to obtain a second solution and a second residue;
8) filtering the second solution from the second residue to obtain a second filtrate;
9) evaporating the second filtrate to remove its solvent and obtain a solute designated as fraction B obtained from the particulate mass;
10) subjecting the second residue to less polar or non-polar solvents, such as petroleum ether, for twelve to thirty-six hours to obtain a third solution and a third residue, and filtering the third solution from the third residue to obtain a third filtrate;
11) evaporating the third filtrate to remove its solvent and obtain a solute designated as fraction C obtained from the particulate mass; and
12) homogeneously mixing the volatile fraction, with fractions A, B and C from the particulate mass to obtain a beneficiated plant extract.

The process is suitable for the preparation of pharmacologically or biologically active plant extracts in a convenient, administrable dosage form from any of the plants mentioned above.

Solvents useful for extracting turmeric include water, ethanol, propanol, paraffin, hexane, petroleum ether, toluene, acetone, methyl ethyl ketone, and other common organic solvents. Water, ethanol and petroleum ether are the preferred solvents for extracting turmeric. Solvents useful for extracting ginger include water, ethanol, propanol, paraffin, petroleum ether, hexane, toluene, acetone, methyl ethyl ketone, and other common organic solvents. Ethanol, water and acetone are the preferred solvents for extracting ginger. Solvents useful for extracting horseradish include water, ethanol, propanol, paraffin, petroleum ether, hexane, toluene, acetone, methyl ethyl ketone, and other common organic solvents. Water and ethanol are the preferred solvents for extracting horseradish.

Most preferably, the nutritional supplement of the present invention includes turmeric extract, ginger root powder, and horseradish root powder, each in a safe and effective amount to provide one or more of the beneficial effects described herein.

Each gram of the nutritional supplement of the present invention preferably contains 5 mg to 20 mg of turmeric powder extract. Most preferably, each gram of the nutritional supplement contains 7 mg to 15 mg of turmeric powder extract.

Each gram of the nutritional supplement of the present invention preferably contains 30 mg to 150 mg of ginger root powder. Most preferably, each gram of the nutritional supplement contains 50 mg to 110 mg of ginger root powder.

Each gram of the nutritional supplement of the present invention preferably contains 25 mg to 70 mg of horseradish root powder. Most preferably, each gram of the nutritional supplement contains 40 mg to 60 mg of horseradish root powder.

Preferably, the nutritional supplement of the present invention may further include a fourth ingredient, namely a suitable demulcent, which may soothe and mobilize mucous membrane in the mouth of a patient. The demulcent may be obtained from slippery elm. Alternatively, the demulcent may be selected from pectin, mucilage and carageenan.

The active compounds of slippery elm, which may be useful in the present invention include, but are not limited to, ascorbic acid, β-carotene, β-sitosterol, citrostadienol, magnesium, manganese, mucilage, niacin, riboflavin, selenium, tannin, thiamin, zinc and mixtures thereof.

Preferably, the fourth ingredient of the nutritional supplement of the present invention, when obtained from slippery elm, is incorporated into the nutritional supplement of the present invention in a form selected from slippery elm bark powder, slippery elm extracts such as slippery elm powder extracts, slippery elm fluid extracts, one or more active compounds of slippery elm, slippery elm bark, tinctures thereof, and mixtures thereof. Slippery elm bark powder may be produced by grinding slippery elm bark. Slippery elm extract may be produced by extracting from slippery elm bark using well-known extraction processes. For a particular active compound, for which a synthetic route is known, the active compound may be synthesized. Alternatively, the slippery elm bark powder, the slippery elm extract and/or the active compounds of slippery elm may be purchased from commercial sources such as Delavau Co.

Preferably, the fourth ingredient of the nutritional supplement of the present invention is selected from slippery elm extract and slippery elm bark powder. More preferably, the fourth ingredient of the nutritional supplement is slippery elm bark powder. Each gram of the nutritional supplement of the present invention preferably contains 50 mg to 150 mg of slippery elm bark powder. Most preferably, each gram of the nutritional supplement contains 75 mg to 120 mg of slippery elm bark powder.

Preferably, the nutritional supplement of the present invention may further include a fifth ingredient, which may be obtained from green tea. The fifth ingredient obtained from green tea may have an antioxidant effect.

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The fifth ingredient of the nutritional supplement of the present invention, which may be obtained from green tea, can be included in the nutritional supplement in the form of green tea powder, green tea extracts such as green tea powder extracts, green tea fluid extracts, and one or more active compounds of green tea, part of, or whole green tea plants, green tea leaves, tinctures thereof, or mixtures thereof. The green tea powder can be produced by grinding dry green tea leaves. The green tea extract may be produced by extracting from dry green tea leaves using common extraction methods. For a particular active compound of green tea, for which a synthetic route is known, the active compound may be synthesized. Alternatively, the green tea powder, the green tea extract and/or the active compounds of green tea can be purchased from commercial sources such as Delavau Co.

Preferably, the fifth ingredient of the nutritional supplement of the present invention is selected from green tea leaves, green tea powder and green tea extract. More preferably, the fifth ingredient of the nutritional supplement of the present invention is green tea extract. Each gram of the nutritional supplement of the present invention preferably contains 5 mg to 20 mg of green tea extract. Most preferably, each gram of the nutritional supplement contains 7 mg to 15 mg of green tea extract.

The nutritional supplement of the present invention may be used for the provision of nutrition by simply ingesting the nutritional supplement, as needed, to provide a nutritional benefit. The nutritional supplement of the present invention may also be employed to promote the health of salivary glands and/or supporting normal or healthy swallowing. By promoting the health of salivary glands, and/or supporting normal or healthy swallowing, the nutritional supplement of the present invention may be useful in improving the quality of life of a person suffering from, for example, sialorrhea or other ailments which impair the health of salivary glands and/or normal or healthy swallowing.

The nutritional supplement of the present invention may also be used as a therapeutic composition to treat one or more of a common cold and/or one or more symptoms thereof, sore throat, congestion, laryngitis, mucositis, and/or mucous membrane inflammation by oral administration to a patient suffering from one or more of these symptoms or ailments. The nutritional supplement of the present invention may also be used to treat sialorrhea caused, for example, by ALS. The nutritional supplement of the present invention may also be used to treat inflammation such as that due to arthritis, based at least in part on the COX-inhibition properties of some of its ingredients such as components obtainable from ginger, turmeric and green tea. The nutritional supplement of the present invention may further be used to treat viral infection. Since the nutritional supplement of the present invention has significant virucidal and virustatic properties as demonstrated by the examples of this application.

In a preferred embodiment, the nutritional supplement of the present invention may further include other natural COX-2 inhibitors such as ingredients obtained from one or more of Chinese goldthread and barberry, holy basil, baikal skullcap, Hu zhang (Japanese Knotweed), rosemary, oregano, feverfew and hops. The additional ingredients which may exhibit COX-2 inhibiting properties include, but are not limited to, one or more of apigenin, baicalein, berberine, catechins, eicosapentaenoic-acid, eugenol, evodiame, evodol, humulone, kaemperol, oleanolic acid, parthenolide, resveratrol, rutaecarpine, salicylic acid, trans-reveratrol and ursolic acid. These additional ingredients can be incorporated in the nutritional supplement of the present invention in the form of a powder, a part of, or a whole plant, a powder extract, a fluid extract, a tincture, when applicable, and mixtures thereof.

The nutritional supplement of the present invention may be formulated using a safe and effective amount of the three main ingredients obtainable from tumeric, ginger and horseradish, to provide one or more of the beneficial effects of the invention described herein, and one or more of the optional ingredients mentioned above, some of which may be obtained from slippery elm or green tea, as well as one or more of the additional optional ingredients described below. The nutritional supplement of the present invention may also be formulated with a pharmaceutically acceptable carrier.

Preferably, the nutritional supplement of the present invention may be formulated in any orally acceptable dosage form including, but not limited to, capsules, tablets, lozenges, troches, hard candies, powders, sprays, gels, elixirs, syrups, and suspensions or solutions.

The pharmaceutically acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex.RTM., Mor-Rex.RTM., Royal-T.RTM., Di-Pac.RTM., Sugar-Tab.RTM., Sweet-Rex.RTM., and New-Tab.RTM.; (b) sugar alcohols including mannitol, sorbitol and xylitol; and (c) various relatively insoluble excipients including dicalcium phosphate, calcium sulfate, calcium carbonate, microcrystalline cellulose and other pharmaceutical tableting ingredients.

Lozenges, tablets, and troches in this invention may differ in shape, size and manufacturing technique. In the case of tablets, for oral use, the pharmaceutically acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common pharmaceutically acceptable carrier may further include a binder such as PEG-8000. Preferably lozenges weigh 0.1 to 15 grams to provide a suitable dissolution rate when taken orally. More preferably, lozenges weigh 1 to 6 grams.

To make compressible lozenges, the active ingredients are added to PEG-8000 processed fructose; or the active ingredients of the nutritional supplement are added to crystalline fructose and commercially available, sweet, direct compression products such as Mendell's Sugartab.RTM., Sweetrex.RTM., or Emdex.RTM. Add sweeteners such as saccharin, if desired, flavors as desired, glidants, such as silica gel, as needed, and lubricants, such as magnesium stearate, as needed. The mixture should be kept dry and tableted soon after mixing. The ingredients are mixed and directly compressed into lozenges using conventional pharmaceutical mixing and tableting equipment. The compressive force is preferably sufficient to produce maximum hardness throughout the lozenges, to preserve a suitable dissolution rate, and to maximize the efficacy of the lozenges. Dissolution of the lozenges, when taken orally, should occur over a sustained period of time, that being 5 to 60 minutes, and preferably about 20 to 30 minutes. The nutritional supplement is preferably stored in an airtight container and in a cool dark place.

Tablets and troches can be manufactured using procedures similar to that described above with minor changes in the optional ingredients. Such changes are within the skill of the ordinary skilled artisan.

Alternatively, the nutritional supplement of the present invention may be formulated in liquid form, such as syrups, mouthwashes or sprays, with a solvent or dispersant such as water, or other liquids and optionally in a pharmaceutically acceptable carrier, for repeated delivery of the nutritional supplement to oral and oropharyngeal mucous membranes over a sustained period of time. Preferably, the treatment time is about 5 to 60 minutes, and more preferably about 20 to 30 minutes, so as to permit a prolonged contact of the nutritional supplement with mouth and throat tissues. Alternatively, such formulations can be in a concentrated form suitable for dilution with water or other materials prior to use.

The nutritional supplement may also be formulated in chewable forms, such as soft candy, gum drops, liquid filled candies, and chewing gum bases, or in the form of dental products, such as toothpastes and mouthwashes. In use, the chewable composition is preferably retained in the mouth over a sustained period of time of preferably about 5 to 60 minutes, and more preferably about 20 to 30 minutes. Dental products may be used in the ordinary manner of using such products.

The nutritional supplement of the invention may be formulated in capsule form, with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The nutritional supplement of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

Other materials, which may optionally be included in the nutritional supplement of the present invention, include inositol, other B-complex vitamins, and anti-inflammatories. Also, ingredients such as sweeteners, flavorants, coloring agents, dyes, preservatives, emulsifying agents, suspending agents, melting agents, excipients, and solvents or diluents such as water, ethanol, propylene glycol, glycerin and various combinations thereof, may be included in the nutritional supplement of the present invention.

The optional sweeteners which may be used in the nutritional supplement of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the nutritional supplement.

The optional flavorants which may be used in the nutritional supplement of the present invention include, but are not limited to, peppermint, peppermint-menthol, eucalyptol, wintergreen, licorice, clove, cinnamon, spearmint, cherry, lemon, orange, lime, menthol and various combinations thereof.

Preferably, the three main ingredients described above which may be derived from turmeric, ginger and horseradish, make up from about 0.5–90% by weight of the total composition of the nutritional supplement. More preferably, the three main ingredients will make up 10–70% by weight of the total composition. Most preferably, the three main ingredients make up 20–40% by weight of the total composition.

The non-carrier ingredients of the nutritional supplement, including the ingredients obtainable from turmeric, ginger, horseradish, slippery elm, and green tea as discussed above, can be increased or decreased proportionally in the nutritional supplement of the present invention depending on the amount of carrier used in the nutritional supplement, without substantially affecting the effectiveness of the nutritional supplement for its intended use.

The present invention also relates to a method of producing a nutritional benefit by administering a nutritional amount of the nutritional supplement of the present invention. The present invention also relates to a method of promoting the health of salivary glands and/or supporting normal or healthy swallowing by administering an effective amount of the nutritional supplement of the present invention.

The nutritional supplement may be administered 1–15 times per day, as needed, more preferably, 2–12 times per day, as needed, or most preferably, 6–10 times per day, as needed. As discussed above, the nutritional supplement of the present invention may be administered to a person in any orally acceptable dosage form including, but not limited to, tablets, capsules, lozenges, troches, hard candies, powders, oral sprays, nasal sprays, gels, elixirs, syrups, chewable compositions, dental products, suspensions, and solutions.

Preferably, during each administration of the nutritional supplement, the nutritional supplement is held in the mouth of the person for at least 5 to 60 minutes to enable the main ingredients of the nutritional supplement to contact the mouth tissue or throat before it completely dissolves. More preferably, the nutritional supplement is held in the mouth of the person for at least 15 to 30 minutes. Preferably, an effective amount of the nutritional supplement for each administration contains a total of 0.1 gram to 1 gram of the three main ingredients, which may be obtained from turmeric, ginger, and horseradish. More preferably, an effective amount of the nutritional supplement for each administration contains a total of 0.2 gram to 0.5 gram of the three main ingredients.

The present invention also relates to a method of administering to a patient an amount of the nutritional supplement of the present invention, which is effective to provide substantial relief of one or more symptoms of a common cold, as well as one or more of a sore throat, congestion, laryngitis, mucositis, mucous membrane inflammation and sialorrhea. In this method, the nutritional supplement of the present invention is used as a therapeutic composition.

The effective amount of the nutritional supplement will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement, and the severity of the illness or symptom. It is within the skill of the person of ordinary skill in the art to account for these factors.

The method of the present invention involves the administration of a composition of the present invention to a patient that suffers from one or more of a common cold, a sore throat, congestion, laryngitis, mucositis, sialorrhea, and mucous membrane inflammation. The nutritional supplement may be administered 1–15 times per day, as needed, more preferably, 2–12 times per day, as needed, or most preferably, 6–10 times per day, as needed. As discussed above, the nutritional supplement of the present invention may be administered to a patient in any orally acceptable dosage form including, but not limited, to tablets, capsules, lozenges, troches, hard candies, powders, oral sprays, nasal sprays, gels, elixirs, syrups, chewable compositions, dental products, suspensions and solutions.

The method of the present invention initially treats acute symptoms but may be continued to provide substantial relief of one or more of a common cold, sore throat, congestion, laryngitis, mucositis, sialorrhea, and mucous membrane inflammation. The method of the present invention may also be employed to prevent the symptoms of a common cold, sore throat, congestion, laryngitis, and mucous membrane inflammation by prophylactic administration of an effective amount of the nutritional supplement.

Preferably, during each therapeutic administration of the nutritional supplement, the nutritional supplement is held in the mouth of the patient for at least 5 to 60 minutes to enable the main ingredients of the nutritional supplement to contact the mouth tissue or throat. More preferably, the nutritional supplement is held in the mouth of the patient for at least 15 to 30 minutes.

Each dosage of the nutritional supplement contains an effective amount of at least the three main ingredients of the nutritional supplement. An effective amount for each therapeutic administration contains a total of 0.1 gram to 1 gram of the three main ingredients, which may be obtained from turmeric, ginger, and horseradish. More preferably, an effective amount of the nutritional supplement for each therapeutic administration contains a total of 0,2 gram to 0.5 gram of the three main ingredients.

Each gram of the nutritional supplement of the present invention preferably contains 5 mg to 20 mg of turmeric powder extract. Most preferably, each gram of the nutritional supplement contains 7 mg to 15 mg of turmeric powder extract. Each gram of the nutritional supplement of the present invention preferably contains 30 mg to 150 mg of ginger root powder. Most preferably, each gram of the nutritional supplement contains 50 mg to 110 mg of ginger root powder. Each gram of the nutritional supplement of the present invention preferably contains 25 mg to 70 mg of horseradish root powder. Most preferably, each gram of the nutritional supplement contains 40 mg to 60 mg of horseradish root powder.

For treatment of sialorrhea, significantly less frequent dosages of the nutritional supplement may be sufficient to provide effective relief. Preferably, 1–6 doses per day are used for sialorrhea. More preferably, only 1–2 doses per day are employed to treat sialorrhea.

In another aspect, the present invention relates to a method of inhibiting the growth of a virus and/or exterminating a virus by administering, to a carrier carrying the virus, a nutritional supplement of the present invention, including ingredients, which can be obtained from turmeric, ginger, and horseradish. In the method, the carrier may be a human, an in vitro cell, or an animal. Preferably, the carrier is a human. In this method, the nutritional supplement of the present invention is used as an antiviral agent and may have one or both of a virustatic effect and a virucidal effect.

In the method, the virus that may be inhibited by the nutritional supplement of the present invention includes, among other viruses, rhinoviruses, Herpes viruses, influenza viruses, HIV-viruses and the West Nile virus. In a preferred embodiment, the viruses that may be inhibited by the nutritional supplement include at least human rhinovirus 16, Herpes I Virus (HSV-1), Influenza A/Moscow/10/99, and B/Guangdong/120/00. By "inhibiting" a virus is meant a reduction or prevention of further growth of the virus, and/or the elimination of some or all of the virus from the human or animal being treated. Suitable methods for determining virus inhibition are discussed in the examples.

The nutritional supplement may be administered 1–15 times per day, as needed, more preferably, 2–12 times per day, as needed, or most preferably, 6–10 times per day, as needed. The nutritional supplement of the present invention may be administered in any orally acceptable dosage form including, but not limited to tablets, capsules, lozenges, troches, hard candies, powders, oral sprays, nasal sprays, gels, elixirs, syrups, chewable compositions, dental products, suspensions, and solutions.

Each dosage of the nutritional supplement contains an effective amount of at least the three main ingredients of the nutritional supplement. An effective amount for each therapeutic administration contains a total of 0.1 gram to 1 gram of the three main ingredients, which may be obtained from turmeric, ginger, and horseradish. More preferably, an effective amount of the nutritional supplement for each therapeutic administration contains a total of 0.2 gram to 0.5 gram of the three main ingredients.

Each gram of the nutritional supplement of the present invention preferably contains 5 mg to 20 mg of turmeric powder extract. Most preferably, each gram of the nutritional supplement contains 7 mg to 15 mg of turmeric powder extract. Each gram of the nutritional supplement of the present invention preferably contains 30 mg to 150 mg of ginger root powder. Most preferably, each gram of the nutritional supplement contains 50 mg to 110 mg of ginger root powder. Each gram of the nutritional supplement of the present invention preferably contains 25 mg to 70 mg of horseradish root powder. Most preferably, each gram of the nutritional supplement contains 40 mg to 60 mg of horseradish root powder.

Preferably, during each administration of the nutritional supplement, the composition is held in the mouth for at least 5 to 60 minutes to enable the main ingredients of the nutritional supplement to contact the mouth tissue or throat before it completely dissolves. More preferably, the nutritional supplement is held in the mouth for at least 15 to 30 minutes.

The present invention also relates to a method of treating a viral infection, or one or more symptoms caused by a viral infection, by administering a nutritional supplement of the present invention, including ingredients which may be obtained from turmeric, ginger, and horseradish.

The symptoms caused by a viral infection which may be treated by this method of the present invention, may include one or more of headache, joint pain, fever, cough, sneezing, muscle ache, running nose, dry mouth, dizziness, and other symptoms related to viral infection. The viral infection may be caused by rhinoviruses including human rhinoviruses, Herpes viruses, such as Herpes I virus (HSV-1), influenza viruses such as Influenza A/Moscow/10/99, and B/Guangdong/120/00, HIV-viruses and the West Nile Virus.

The nutritional supplement may be administered 1–15 times per day, as needed, more preferably, 2–12 times per day, as needed, or most preferably, 6–10 times per day, as needed. The nutritional supplement of the present invention may be administered in any orally acceptable dosage form including, but not limited to tablets, capsules, lozenges, troches, hard candies, powders, oral sprays, nasal sprays, gels, elixirs, syrups, chewable compositions, dental products, suspensions, and solutions.

Preferably, during each administration of the nutritional supplement, the nutritional supplement is held in the mouth for at least 5 to 60 minutes to enable the main ingredients of the nutritional supplement to contact the mouth tissue or throat. More preferably, the nutritional supplement is held in the mouth for at least 15 to 30 minutes.

Each dosage of the nutritional supplement contains an effective amount of at least the three main ingredients of the nutritional supplement. An effective amount for each therapeutic administration contains a total of 0.1 gram to 1 gram of the three main ingredients, which may be obtained from turmeric, ginger, and horseradish. More preferably, an effective amount of the nutritional supplement for each therapeutic administration contains a total of 0.2 gram to 0.5 gram of the three main ingredients.

Each gram of the nutritional supplement of the present invention preferably contains 5 mg to 20 mg of turmeric powder extract. Most preferably, each gram of the nutritional supplement contains 7 mg to 15 mg of turmeric powder extract. Each gram of the nutritional supplement of the present invention preferably contains 30 mg to 150 mg of ginger root powder. Most preferably, each gram of the nutritional supplement contains 50 mg to 110 mg of ginger root powder. Each gram of the nutritional supplement of the present invention preferably contains 25 mg to 70 mg of horseradish root powder. Most preferably, each gram of the nutritional supplement contains 40 mg to 60 mg of horseradish root powder.

In another aspect, the present invention relates to a method of treating one or more symptoms of inflammation, which may be caused by, for example, arthritis, by administering a nutritional supplement in accordance with the present invention, including ingredients, which can be obtained from turmeric, ginger, and horseradish, as a therapeutic composition. The symptoms of inflammation may include one or more of joint pain, joint immobility, and joint stiffness.

It has been found that the nutritional supplement of the present invention has analgesic properties due to its COX-2 inhibiting and anti-inflammatory properties. The nutritional supplement of the present invention can be used to relieve the pain or other symptoms caused by human arthritis or similar afflictions which cause inflammation. To relieve the symptoms of arthritis, the nutritional supplement may be administered 1–15 times per day, as needed, more preferably, 2–12 times per day, as needed, or most preferably, 6–10 times per day, as needed. As discussed above, the nutritional supplement of the present invention may be administered in any orally acceptable dosage form including, but not limited to tablets, capsules, lozenges, troches, hard candies, powders, oral sprays, nasal sprays, gels, elixirs, syrups, chewable compositions, dental products, suspensions, and solutions.

Preferably, during each administration of the nutritional supplement, it is held in the mouth for at least 5 to 60 minutes to enable the main ingredients contact the mouth tissue or throat. More preferably, the nutritional supplement is held in the mouth for at least 15 to 30 minutes.

Each dosage of the nutritional supplement contains an effective amount of at least the three main ingredients of the nutritional supplement. An effective amount for each therapeutic administration contains a total of 0.1 gram to 1 gram of the three main ingredients, which may be obtained from turmeric, ginger, and horseradish. More preferably, an effective amount of the nutritional supplement for each therapeutic administration contains a total of 0.2 gram to 0.5 gram of the three main ingredients.

Each gram of the nutritional supplement of the present invention preferably contains 5 mg to 20 mg of turmeric powder extract. Most preferably, each gram of the nutritional supplement contains 7 mg to 15 mg of turmeric powder extract. Each gram of the nutritional supplement of the present invention preferably contains 30 mg to 150 mg of ginger root powder. Most preferably, each gram of the nutritional supplement contains 50 mg to 110 mg of ginger root powder. Each gram of the nutritional supplement of the present invention preferably contains 25 mg to 70 mg of horseradish root powder. Most preferably, each gram of the nutritional supplement contains 40 mg to 60 mg of horseradish root powder.

Each of the various methods of the present invention may be applied with humans or animals. The invention will be further illustrated by the examples given below which are not to be construed as limiting the invention in any way. The scope of the invention is to be determined by the claims appended hereto.

EXAMPLES

Example 1

A Nutritional Supplement of the Present Invention

A nutritional supplement of the present invention formulated in the form of lozenges was prepared using the procedure described above. The ingredients of the lozenge are listed below:

| | |
|---|---|
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

Example 2

Treatment of Sore Throat

Each of seven patients, suffering from sore throats, ingested one lozenge of Example 1 every two hours by holding the lozenge in his or her mouth for about 15–30 minutes until the lozenge completely dissolved. No patient took more than 10 lozenges in any given day.

The patients, that were treated, reported complete relief from the symptoms of their sore throats after ingesting from 2 to 20 lozenges. It was also found that each lozenge can provide relief from a sore throat for up to 6 hours.

Example 3

Treatment of Sialorrhea

Two patients, who suffer from sialorrhea caused by ALS, ingested 1–2 lozenges of Example 1 every day for a three-week period. It was found that the ingestion of the lozenges effectively controlled excessive secretions of saliva in these two patients. In both patients, excessive drooling was also significantly reduced.

Example 4

In Vitro Testing of Virucidal Activity of the Nutritional Supplement

The in vitro testing protocol for virucidal activity employed in this example uses human rhinovirus 16 (hereafter "HRV-16") as the target virus, and the MRC-5 cell line related to human tissues described by Jacobs, et al, *Characteristics of Human diploid MRC-5*, Nature (London), 227, p168–170 (1970) as the host cell for the HRV-16 viruses. Residual virus infectivity following incubation of the test substances with the virus was titrated on the MRC-5 cell line for rhinovirus growth by visually scoring the cytopathic effect (CPE) induced by virus replication through microscopic observation. More specifically, CPE was scored by observing ballooning/rounded cells in the MRC-5 culture.

To determine the virucidal activity, the nutritional supplement composition of Example 1 (hereafter "Substance 1"), was employed at an initial dilution of 1/20 and then further diluted by serial dilutions in saline. The diluted compositions were incubated with HRV-16 for a set time period and then the reaction was terminated by adjustment to a neutral pH with cell infection media. The resultant solution was then titrated out on MRC-5 cells at a dilution of 1/10 across a testing plate to carry out the infection of the cells. Each plate housed a virus control, which contained only HRV-16 infected MRC-5 cells, and a cell control, which contained only uninfected MRC-cells.

The plates were further incubated for 4 days after the infection. Residual viral infectivity was measured using the assay discussed above. From the results shown in Tables 1–4, all of the controls on the plate worked well.

From the assay, it was concluded that Substance 1, at a 1/20 dilution, was effective in producing an HRV-16 viral log reduction of 1.50 (–log 10 TCID50) at the 1-minute incubation period. A 1/40 dilution of Substance 1 produced a log reduction of 1.00 (–log 10 TCID50) also at the 1-minute incubation period. After the 2-minute and 5-minute incubation periods, ½ log reductions in HRV-16 titre were achieved. Therefore, these results tend to indicate that a 1-minute contact time between Substance 1 and HRV-16 would produce the most effective viral titre reduction.

Table 1 shows the residual virus titres and log reductions of infectious Rhinovirus 16 on MRC-5 cells at one termination time point, of Substance 1 at different dilutions.

TABLE 1

| | pH value of Substance 1 in Isotonic solution | pH value of terminated solution | Virus Control (TCID50) | 1 Minute Incubation | |
|---|---|---|---|---|---|
| Dilutions | | | | Residual Virus titer (TCID50) | Log Reductions (TCID50) |
| 1/20 | 5.03 | 7.73 | 3.80 | 2.30 | 1.50 |
| 1/40 | 5.13 | 7.77 | 3.80 | 3.30 | 0.50 |
| 1/80 | 4.98 | 7.83 | 3.80 | 3.80 | 0.00 |

TABLE 1-continued

| Dilutions | pH value of Substance 1 in Isotonic solution | pH value of terminated solution | Virus Control (TCID50) | Residual Virus titer (TCID50) | Log Reductions (TCID50) |
|---|---|---|---|---|---|
| 1/160 | 4.98 | 7.73 | 3.80 | 3.80 | 0.00 |

Tables 2–4 show the results of a second trial on the residual virus titres and the log reductions of infectious HRV-16 on MRC-5 cells at three different termination time points, of Substance 1 at different dilutions.

TABLE 2

1 Minute Incubation

| Dilutions of Substance 1 | HRV-16 Control Titer (TCID50) | Residual HRV-16 titer (TCID50) | HRV-16 log Reductions (TCID50) |
|---|---|---|---|
| 1/20 | 3.30 | 1.80 | 1.50 |
| 1/40 | 3.30 | 2.30 | 1.00 |
| 1/80 | 3.30 | 2.80 | 0.50 |
| 1/160 | 3.30 | 2.80 | 0.50 |
| 1/320 | 3.30 | 2.80 | 0.50 |

TABLE 3

2 Minute Incubation

| Dilutions of Substance 1 | HRV-16 Control Titer (TCID50) | Residual HRV-16 titer (TCID50) | HRV-16 log Reductions (TCID50) |
|---|---|---|---|
| 1/20 | 3.30 | 2.80 | 0.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |

TABLE 4

5 Minute Incubation

| Dilutions of Substance 1 | HRV-16 Control Titer (TCID50) | Residual HRV-16 titer (TCID50) | HRV-16 log Reductions (TCID50) |
|---|---|---|---|
| 1/20 | 3.30 | 2.80 | 0.50 |
| 1/40 | 3.30 | 2.80 | 0.50 |
| 1/80 | 3.30 | 3.30 | 0.00 |
| 1/160 | 3.30 | 2.80 | 0.50 |
| 1/320 | 3.30 | 2.80 | 0.50 |

Similar virucidal tests have been carried out for Substance 1 using other viruses, including Herpes I Virus (HSV-1) using Vero cells as the host cell, Influenza A/Moscow/10/99, and B/Guangdong/120/00 using MDCK cells as the host cell. The results on these virucidal tests are summarized below in Tables 5–13.

Tables 5–7 show the residual virus titres and log reductions of infectious HSV-1 on Vero cells at three different termination time points, of Substance 1 at different dilutions.

TABLE 5

1 Minute Incubation

| Dilutions of Substance 1 | HSV-1 Control Titer (−log 10 TCID50) | Residual HSV-1 titer (−log 10 TCID50) | HSV-1 log reductions (−log 10 TCID50) |
|---|---|---|---|
| 1/40 | 3.80 | 0.00 | 3.80 |
| 1/80 | 3.80 | 0.00 | 3.80 |
| 1/160 | 3.80 | 2.80 | 1.00 |
| 1/320 | 3.80 | 2.80 | 1.00 |
| 1/640 | 3.80 | 2.80 | 1.00 |

TABLE 6

2 Minute Incubation

| Dilutions of Substance 1 | HSV-1 Control Titer (−log 10 TCID50) | Residual HSV-1 titer (−log 10 TCID50) | HSV-1 log reductions (−log 10 TCID50) |
|---|---|---|---|
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

TABLE 7

5 Minute Incubation

| Dilutions of Substance 1 | HSV-1 Control Titer (−log 10 TCID50) | Residual HSV-1 titer (−log 10 TCID50) | HSV-1 log reductions (−log 10 TCID50) |
|---|---|---|---|
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

Tables 8–10 show the residual virus titres and log reductions of influenza A/Moscow/10/99 at three different termination time points, of Substance 1 at different dilutions.

TABLE 8

1 Minute Incubation

| Dilutions of Substance 1 | A/Moscow Virus Titer (−log 10 TCID50) | Residual A/Moscow titer (−log 10 TCID50) | A/Moscow log reductions (−log 10 TCID50) |
|---|---|---|---|
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 9

| | | 2 Minute Incubation | |
|---|---|---|---|
| Dilutions of Substance 1 | A/Moscow Virus Titer (–log 10 TCID50) | Residual A/Moscow titer (–log 10 TCID50) | A/Moscow log reductions (–log 10 TCID50) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 10

| | | 5 Minute Incubation | |
|---|---|---|---|
| Dilutions of Substance 1 | A/Moscow Virus Titer (–log 10 TCID50) | Residual A/Moscow titer (–log 10 TCID50) | A/Moscow log reductions (–log 10 TCID50) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 0.00 | 2.80 |

Tables 11–13 show the residual virus titres and log reductions of Influenza B/Guangdong/120/00 at three different termination time points, of Substance 1 at different dilutions.

TABLE 11

| | | 1 Minute Incubation | |
|---|---|---|---|
| Dilutions of Substance 1 | B/Guangdong Virus Titer (-log 10 TCID50) | Residual B/Guangdong titer (-log 10 TCID50) | B/Guangdong log reductions (-log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.30 | -0.50 |
| Citrate Buffer | 1.80 | 0.00 | 1.80 |

TABLE 12

| | | 2 Minute Incubation | |
|---|---|---|---|
| Dilutions of Substance 1 | B/Guangdong Virus Titer (-log 10 TCID50) | Residual B/Guangdong titer (-log 10 TCID50) | B/Guangdong log reductions (-log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.80 | -1.00 |

TABLE 12-continued

| | | 2 Minute Incubation | |
|---|---|---|---|
| Dilutions of Substance 1 | B/Guangdong Virus Titer (-log 10 TCID50) | Residual B/Guangdong titer (-log 10 TCID50) | B/Guangdong log reductions (-log 10 TCID50) |
| Citrate Buffer | 1.80 | 0.00 | 1.80 |

TABLE 13

| | | 5 Minute Incubation | |
|---|---|---|---|
| Dilutions of Substance 1 | B/Guangdong Virus Titer (-log 10 TCID50) | Residual B/Guangdong titer (-log 10 TCID50) | B/Guangdong log reductions (-log 10 TCID50) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.80 | -1.00 |
| Citrate Buffer | 1.80 | 0.00 | 1.80 |

In Tables 1–13, TCID50=–log 10 TCID50.

As one can see from above results, Substance 1 is effective in inhibiting or exterminating influenza viruses and human rhinoviruses. As a result, Substance 1 should be effective in treating influenza and common colds.

Example 5

In Vitro Testing of Virustatic Activity of the Nutritional Supplement

The in vitro testing protocol for virucidal activity employed in this example used human rhinovirus 16 (HRV-16) as the target virus, and the rhinovirus sensitive Hela cell line related to human tissues described by Conant et al, *Basis for a numbering system. I. Hela cells for propagation and serologic procedure*, J. Immunol., 100, p107–113 (1968) as the host cell for the HRV-16 virus.

The nutritional supplement of Example 1, Substance 1, was dissolved in infection media to the following dilutions: 1/20, 1/40, 1/80, 1/160 and 1/320. These dilutions were incubated on plates of MRC-5 cells for 30 minutes at 37° C. (5% $CO_2$). After the incubation period, each Substance 1 dilution with MRC-5 cells in a well of the plates was subjected to HRV-16 at a known titre of 2.30 (–log 10 TCID50). Each plate housed a virus control (the Hela cells infected with HRV-16 viruses and without Substance 1), a cell control (Hela cells only) and the test compound controls at the different dilutions (Hela cells with the test substance only). All the other samples on the plate contained the Hela cells infected with HRV-16 viruses and Substance 1 at different dilutions. The plates were further incubated for 4 days after infection.

Residual virus infectivity following incubation of Substance 1 with the virus was titrated on the Hela cell line for rhinovirus growth by measuring the cytopathic effect (CPE) induced by the virus using the following procedure.

The remaining viable Hela cells after incubation with Substance 1 were stained with crystal violet solution. Excess crystal violet was removed by washing and the crystal violet stained cells were solubilized using a mixture of methanol and acetic acid. The absorbance of the solution was then measured at 540 nm in an ELISA plate reader. The level of virus induced CPE was inversely proportional to the absorbance.

The results generated from the crystal violet assay enabled the toxic concentration and the effective concentration of Substance 1 to be determined by fitting an equation, y=mx+c, wherein x corresponds to the dilution of Substance 1 and y corresponds to percentage of toxicity of Substance 1 to the cells. From this equation, the TC50 (concentration at which Substance 1 indicates 50% toxicity to the cells) is at a 1/571 dilution of Substance 1.

This result correlates well with the percentage of cell survivors at various dilution of Substance 1, which was also measured using the crystal violet assay, as shown in Table 14 below.

TABLE 14

| Dilution of Substance 1 without Virus | % Cell Survivors |
|---|---|
| 1/320 | 89.7 |
| 1/160 | 94.6 |
| 1/80 | 97.6 |
| 1/40 | 109.3 |
| 1/20 | 168.2 |

Using the same equation, wherein x still corresponds to the dilution of Substance 1 and y corresponds to the percent efficacy of Substance 1 in the presence of the virus, the EC50 (concentration at which the test substance indicates 50% efficacy in the presence of virus) was determined to be at a 1/91 dilution of Substance 1. This result correlates well with the percentage of viable cells at various dilutions of Substance 1 measured using the crystal violet assay, as shown in Table 15 below.

TABLE 15

| Substance 1 dilution and Virus | % Viable Cells |
|---|---|
| 1/320 + HRV-16 | 79.3 |
| 1/160 + HRV-16 | 62.3 |
| 1/80 + HRV-16 | 39.0 |
| 1/40 + HRV-16 | 15.9 |
| 1/20 + HRV-16 | −220.0 |

In Tables 14 and 15, % Cell Survivors=(Compound only/Cell only)×100; and % Viable Cells=(Cell only−Compound+Virus)/(Cell only−Virus only)×100.

"Compound only" denotes the measurement results for the wells containing only Hela cells and Substance 1 at a predetermined dilution.

"Cell only" denotes the measurement results for the wells containing only uninfected Hela cells.

"Compound+Virus" denotes the measurement results for the wells containing both the Hela cells infected with HRV-16 viruses and Substance 1 at a predetermined dilution.

"Virus Only" denotes the measurement results for the wells containing the Hela cells infected with HRV-16 only.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

We claim:

1. A method for treating at least one symptom of arthritis comprising the step of administering an effective amount of a nutritional supplement comprising
   a first ingredient obtainable from turmeric;
   a second ingredient obtainable from ginger; and
   a third ingredient obtainable from horseradish,
   to a human or animal suffering from arthritis.

2. A method as claimed in claim 1, wherein the symptom is inflammation due to arthritis.

3. A method as claimed in claim 2, wherein the step of administering the nutritional supplement comprises the step of retaining the nutritional supplement in the mouth for a period of from about 5 to about 60 minutes.

4. A method as claimed in claim 2, wherein the step of retaining the nutritional supplement in the mouth is carried out for a period of from about 15 to about 30 minutes.

5. A method as claimed in claim 2, wherein the step of administering the nutritional supplement to the person is carried out 1 to 15 times per day.

6. A method as claimed in claim 2, wherein the step of administering the nutritional supplement is carried out 2–12 times per day.

7. A method as claimed in claim 2, wherein the step of administering the nutritional supplement is carried out 6–10 times per day.

8. A method as claimed in claim 6, wherein the step of administering the nutritional supplement comprises the step of retaining the nutritional supplement in the mouth for a period of from about 5 to about 60 minutes.

9. A method as claimed in claim 8, wherein the nutritional supplement is administered in a form selected from the group consisting of lozenges, troches, hard candies, and 10. A method as claimed in claim 2, wherein the nutritional supplement is administered in a form selected from the group consisting of tablets, capsules, lozenges, troches, hard candies, powders, oral sprays, nasal sprays, gels, elixirs, syrups, chewable compositions, dental products, liquid suspensions and liquid solutions.

11. A method as claimed in claim 10, wherein the nutritional supplement contains, as an effective amount for each therapeutic administration, a total of 0.1–1 gram of the ingredients obtainable from turmeric, ginger, and horseradish.

12. A method as claimed in claim 10, wherein the nutritional supplement contains, as an effective amount for each administration, a total of 0.2–0.5 grain of the ingredients obtainable from turmeric, ginger and horseradish.

13. A method as claimed in claim 10, wherein the nutritional supplement contains, based on 1 gram of nutritional supplement, 5 mg to 20 mg of turmeric powder extract, 30 mg to 150 mg of ginger root powder, and 25 mg to 70 mg of horseradish root powder.

14. A method as claimed in claim 10, wherein each gram of the nutritional supplement contains 40 mg to 60 mg of horseradish root powder.

15. A method as claimed in claim 10, wherein each gram of the nutritional supplement contains 7 mg to 15 mg of turmeric powder extract.

16. A method as claimed in claim 10, wherein each gram of the nutritional supplement contains 50 mg to 110 mg of ginger root powder.

17. A method as claimed in claim 2, wherein the nutritional supplement further comprises an ingredient obtainable from slippery elm.

18. A method as claimed in claim 2, wherein the nutritional supplement further comprises an ingredient obtainable from green tea.

19. A method as claimed in claim 2, wherein the nutritional supplement is administered to a patient suffering from one or more of joint pain, joint immobility and joint stiffness.

20. A method as claimed in claim 13, wherein the step of administering the nutritional supplement is carried out 2–12 times per day.

* * * * *

UNITED STATES PATENT AND TRADEMARK OFFICE
CERTIFICATE OF CORRECTION

PATENT NO.     : 6,827,945 B2
DATED          : December 7, 2004
INVENTOR(S)    : Richard A. Rosenbloom It is certified that error appears in the above-identified patent and that said Letters Patent is hereby corrected as shown below:

<u>Title page,</u>
Item [57], ABSTRACT,
Line 8, please change "viral infectin" to -- viral infection --.

Signed and Sealed this

Twelfth Day of April, 2005

JON W. DUDAS
*Director of the United States Patent and Trademark Office*